(12) United States Patent
Pulé et al.

(10) Patent No.: US 11,945,867 B2
(45) Date of Patent: Apr. 2, 2024

(54) T-CELL RECEPTOR CONSTANT REGION 1 ANTIBODY OR T-CELL RECEPTOR CONSTANT REGION 2 ANTIBODY

(71) Applicant: AUTOLUS LIMITED, London (GB)

(72) Inventors: Martin Pulé, London (GB); Shimobi Onuoha, London (GB); Ana Margarida Neves, London (GB); Mathieu Ferrari, London (GB); Paul Maciocia, London (GB)

(73) Assignee: AUTOLUS LIMITED, London (GB)

( * ) Notice: Subject to any disclaimer, the term of this patent is extended or adjusted under 35 U.S.C. 154(b) by 602 days.

(21) Appl. No.: 17/287,307

(22) PCT Filed: Dec. 21, 2019

(86) PCT No.: PCT/GB2019/053000
§ 371 (c)(1),
(2) Date: Apr. 21, 2021

(87) PCT Pub. No.: WO2020/084290
PCT Pub. Date: Apr. 30, 2020

(65) Prior Publication Data
US 2021/0355217 A1    Nov. 18, 2021

(30) Foreign Application Priority Data
Oct. 22, 2018   (GB) .................................. 1817172

(51) Int. Cl.
*C07K 16/28*  (2006.01)
*G01N 33/574* (2006.01)

(52) U.S. Cl.
CPC ... *C07K 16/2809* (2013.01); *G01N 33/57426* (2013.01); *C07K 2317/10* (2013.01); *C07K 2317/33* (2013.01); *G01N 2333/7051* (2013.01)

(58) Field of Classification Search
None
See application file for complete search history.

(56) References Cited

U.S. PATENT DOCUMENTS

| | | |
|---|---|---|
| 2014/0308250 A1 | 10/2014 | Handgretinger et al. |
| 2017/0066827 A1 | 3/2017 | Pulé et al. |
| 2017/0334998 A1 | 11/2017 | Pulé et al. |
| 2018/0086831 A1 | 3/2018 | Pulé et al. |
| 2019/0209612 A1 | 7/2019 | Pulé et al. |
| 2020/0140549 A1 | 5/2020 | Cordoba et al. |
| 2020/0200756 A1 | 6/2020 | Pulé et al. |

FOREIGN PATENT DOCUMENTS

| | | |
|---|---|---|
| EP | 0403156 A1 | 12/1990 |
| WO | WO-2012/038055 A1 | 3/2012 |
| WO | WO-2015/132598 A1 | 9/2015 |
| WO | WO-2016/051205 A1 | 4/2016 |
| WO | WO-2018/224844 A1 | 12/2018 |
| WO | WO-2020/025928 A1 | 2/2020 |
| WO | WO-2020/089644 A1 | 5/2020 |

OTHER PUBLICATIONS

International Search Report and Written Opinion from International Application No. PCT/GB2019/05300 dated Jan. 23, 2020.
Maciocia et al., "Targeting the T cell receptor B-chain constant region for immunotherapy of T cell malignancies," Nature Medicine 23(12):1416-1423 (2017).
U.S. Appl. No. 16/353,068, filed Mar. 14, 2019.
U.S. Appl. No. 16/664,190, filed Oct. 25, 2019.
U.S. Appl. No. 17/264,217, filed Jan. 28, 2021.
U.S. Appl. No. 17/290,188, filed Apr. 29, 2021.

*Primary Examiner* — Zachary S Skelding
(74) *Attorney, Agent, or Firm* — MARSHALL, GERSTEIN & BORUN LLP

(57) ABSTRACT

The present invention provides antibodies and polyclonal antibody preparations which bind the intracellular portion of either T-cell receptor constant region 2 (TRBC2) or T-cell receptor constant region 1 (TRBC1). The antibodies can be used to determine whether a T-cell malignancy clonally expresses TRBC1 or TRBC2.

11 Claims, 5 Drawing Sheets

Specification includes a Sequence Listing.

FIGURE 3

```
TRBC1   1 EDLNKVFPPEVAVFEPSEAEISHTQKATLVCLATGFFPDHVELSWWVNGK
TRBC2   1 EDLKNVFPPEVAVFEPSEAEISHTQKATLVCLATGFYPDHVELSWWVNGK
                    ------Extracellular------

TRBC1  51 EVHSGVSTDPQPLKEQPALNDSRYCLSSRLRVSATFWQNPRNHFRCQVQF
TRBC2  51 EVHSGVSTDPQPLKEQPALNDSRYCLSSRLRVSATFWQNPRNHFRCQVQF
                    ------Extracellular------

TRBC1 101 YGLSENDEWTQDRAKPVTQIVSAEAWGRADCGFTSVSYQQGVLSATILYE
TRBC2 101 YGLSENDEWTQDRAKPVTQIVSAEAWGRADCGFTSESYQQGVLSATILYE
                    ------Extracellular------

TRBC1 151 ILLGKATLYAVLVSALVLMAMVKRKDF--
TRBC2 151 ILLGKATLYAVLVSALVLMAMVKRKDSRG
          ---Transmembrane---|---Intracellular---
```

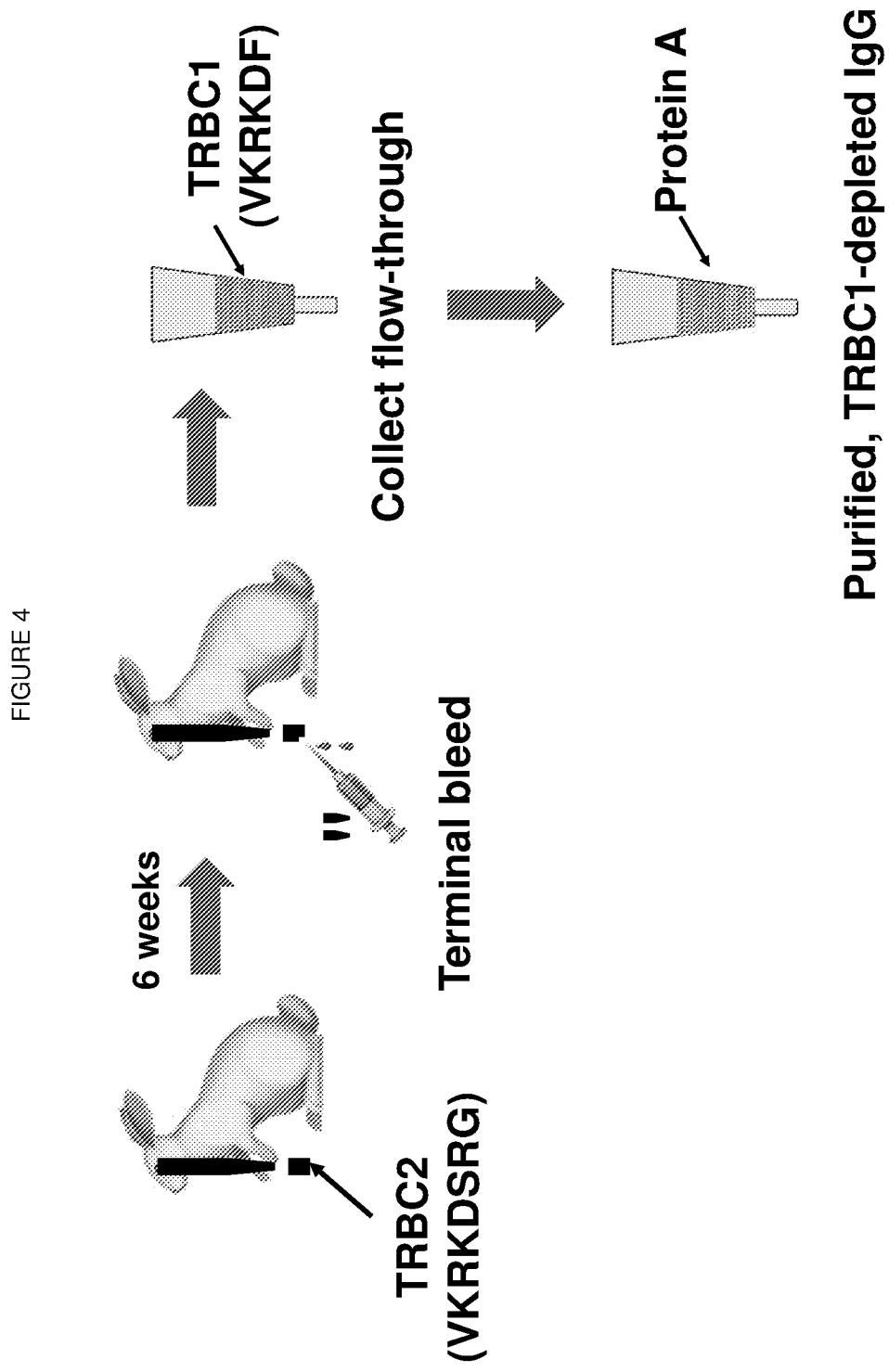

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: T-cell receptor constant region 2 (TRBC2)
      intracellular portion sequence

<400> SEQUENCE: 1

Val Lys Arg Lys Asp Ser Arg Gly
1               5

<210> SEQ ID NO 2
<211> LENGTH: 6
<212> TYPE: PRT
<213> ORGANISM: Artificial Sequence
<220> FEATURE:
<223> OTHER INFORMATION: T-cell receptor constant region 1 (TRBC1)
      intracellular portion sequence

<400> SEQUENCE: 2

Val Lys Arg Lys Asp Phe
1               5

<210> SEQ ID NO 3
<211> LENGTH: 7
<212> TYPE: PRT
<213> ORGANISM: Artificial Sequence
<220> FEATURE:
<223> OTHER INFORMATION: variable heavy chain (VH) complementarity
      determining region (CDR), VH CDR1

<400> SEQUENCE: 3

Gly Tyr Thr Phe Thr Gly Tyr
1               5

<210> SEQ ID NO 4
<211> LENGTH: 6
<212> TYPE: PRT
<213> ORGANISM: Artificial Sequence
<220> FEATURE:
<223> OTHER INFORMATION: VH CDR2

<400> SEQUENCE: 4

Asn Pro Tyr Asn Asp Asp
1               5

<210> SEQ ID NO 5
<211> LENGTH: 15
<212> TYPE: PRT
<213> ORGANISM: Artificial Sequence
<220> FEATURE:
<223> OTHER INFORMATION: VH CDR3

<400> SEQUENCE: 5

Gly Ala Gly Tyr Asn Phe Asp Gly Ala Tyr Arg Phe Phe Asp Phe
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: variable light chain (VL) CDR, VL CDR1

<400> SEQUENCE: 6
```

Arg Ser Ser Gln Arg Leu Val His Ser Asn Gly Asn Thr Tyr Leu His
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: VL CDR2

<400> SEQUENCE: 7

Arg Val Ser Asn Arg Phe Pro
1               5

<210> SEQ ID NO 8
<211> LENGTH: 9
<212> TYPE: PRT
<213> ORGANISM: Artificial Sequence
<220> FEATURE:
<223> OTHER INFORMATION: VL CDR3

<400> SEQUENCE: 8

Ser Gln Ser Thr His Val Pro Tyr Thr
1               5

<210> SEQ ID NO 9
<211> LENGTH: 177
<212> TYPE: PRT
<213> ORGANISM: Homo sapiens

<400> SEQUENCE: 9

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Val Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 10
<211> LENGTH: 179
<212> TYPE: PRT
<213> ORGANISM: Homo sapiens

```
<400> SEQUENCE: 10

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
            85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
            165                 170                 175

Ser Arg Gly
```

T-CELL RECEPTOR CONSTANT REGION 1 ANTIBODY OR T-CELL RECEPTOR CONSTANT REGION 2 ANTIBODY

CROSS-REFERENCE TO RELATED APPLICATIONS

This is a U.S. National Phase of International Application No. PCT/GB2019/053000, filed Oct. 21, 2019, which claims priority to Great Britain Application No. 1817172.8 filed Oct. 22, 2018.

FIELD OF THE INVENTION

The invention relates to antibodies and antibody preparations which bind T-cell receptor constant region 1 (TRBC1) or T-cell receptor constant region 2 (TRBC2). The antibodies and antibody preparations may be used to investigate the T-cell clonality of a T-cell malignancy in a subject.

BACKGROUND TO THE INVENTION

T-Cell Malignancies

Lymphoid malignancies can largely be divided into those which are derived from either T-cells or B-cells. T-cell malignancies are a clinically and biologically heterogeneous group of disorders, together comprising 10-20% of non-Hodgkin's lymphomas and 20% of acute leukaemias. The most commonly identified histological subtypes are peripheral T-cell lymphoma, not otherwise specified (PTCL-NOS); angio-immunoblastic T-cell lymphoma (AITL) and anaplastic large cell lymphoma (ALCL). Of all acute Lymphoblastic Leukaemias (ALL), some 20% are of a T-cell phenotype.

These conditions typically behave aggressively, compared for instance with B-cell malignancies, with estimated 5-year survival of only 30%. In the case of T-cell lymphoma, they are associated with a high proportion of patients presenting with disseminated disease, unfavourable International Prognostic Indicator (IPI) score and prevalence of extra-nodal disease. Chemotherapy alone is not usually effective and less than 30% of patients are cured with current treatments.

Further, unlike in B-cell malignancies, where immunotherapies such as the anti-CD20 monoclonal antibody rituximab have dramatically improved outcomes, there is currently no equivalently effective, minimally toxic immunotherapeutic available for the treatment of T-cell malignancies. An important difficulty in the development of immunotherapy for T-cell disorders is the considerable overlap in marker expression of clonal and normal T-cells, with no single antigen clearly able to identify clonal (malignant) cells.

The same problem exists when targeting a pan-B-cell antigen to treat a B-cell malignancy. However, in this case, the concomitant depletion of the B-cell compartment results in relatively minor immunosuppression which is readily tolerated by most patients. Further, in therapies which result in particularly long-term depletion of the normal B-compartment, its loss can be largely abrogated by administration of pooled immunoglobulin. The situation is completely different when targeting T-cell malignancies. Here, concomitant depletion of the T-cell compartment leads to severe immunosuppression and severe toxicity. Further, there is no satisfactory way to mitigate loss of the T-cell compartment.

The toxicity is in part illustrated by the clinical effects of the therapeutic monoclonal antibody Alemtuzumab. This agent lyses cells which express CD52 and has some efficacy in T-cell malignancies. The utility of this agent is greatly limited by a profound cellular immunodeficiency, largely due to T-cell depletion, with markedly elevated risk of infection.

T-Cell Receptor Constant Region

The T-cell receptor (TCR) is expressed on the surface of T lymphocytes and is responsible for recognizing antigens bound to major histocompatibility complex (MHC) molecules. The TCR is a disulfide-linked membrane-anchored heterodimer normally consisting of the highly variable alpha (α) and beta (β) chains expressed as part of a complex with the invariant CD3 chain molecules. The TCR α and β chains are composed of amino-terminal variable and carboxy-terminal constant regions.

The locus (Chr7:q34) which supplies the TCR β-constant region (TRBC) has duplicated in evolutionary history to produce two almost identical and functionally equivalent genes: TRBC1 and TRBC2. T cell malignancies are clonal, so they either express TRBC1 or TRBC2 (Maciocia et al (2017) Nature Medicine 2017 23(12): 1416-1423).

WO2015/132598 describes agents, such as chimeric antigen receptors (CARs), which selectively bind TRBC1 or TRBC2. Such agents are useful in methods for treating a T-cell lymphoma or leukaemia in a subject. By administering a TCRB1 or TCRB2 selective agent to the subject, the agent causes selective depletion of the malignant T-cells, together with normal T-cells expressing the same TRBC as the malignant T-cells. However, the agent does not cause depletion of normal T-cells expressing the other TRBC, i.e. the TRBC not expressed by the malignant T-cells.

Since the TRBC selective agent spares normal T-cells expressing the other TRBC from the malignant T-cells, it does not cause depletion of the entire T-cell compartment. Retention of a proportion of the subject's T-cell compartment (i.e. T-cells which do not express the same TRBC as the malignant T-cell) is sufficient to provide cellular and humoral immunity for the subject.

In order to determine the correct therapy for a patient having a T-cell malignancy, it is necessary to establish the malignant T cells clonally expresses TRBC1 or TRBC2 in that patient.

Maciocia et al (as above) describe an antibody, known as JOVI-1, which specifically binds TRBC1. JOVI-1 selectively binds TRBC1-expressing cells and can be used to determine whether T-cell derived malignant cell lines and primary T-cell tumours are clonally TRBC1+ or TRBC1-.

The residues of TRBC responsible for the TRBC1 specificity of JOVI-1 have been determined to be the asparagine (N)/lysine(K)-→KN difference at residues 3 and 4.

JOVI-1 has been used to investigate T-cell clonality of frozen tissue sections using techniques such as flow cytometry (FACS) or immunohistochemistry (IHC). A disadvantage of JOVI-1 is that it does not work on fixed tissue, for example formalin-fixed paraffin-embedded (FFPE) tissue samples.

There is therefore a need to provide alternative diagnostic agents to investigate the TRBC1/TRBC2 clonality of T-cell malignancies.

DESCRIPTION OF THE FIGURES

FIG. 3: Alignment of human TRBC1 and TRBC2 at the amino acid level.

FIG. 4: Method for TRBC2-specific polyclonal antibody preparation

SUMMARY OF ASPECTS OF THE INVENTION

Figure 1:
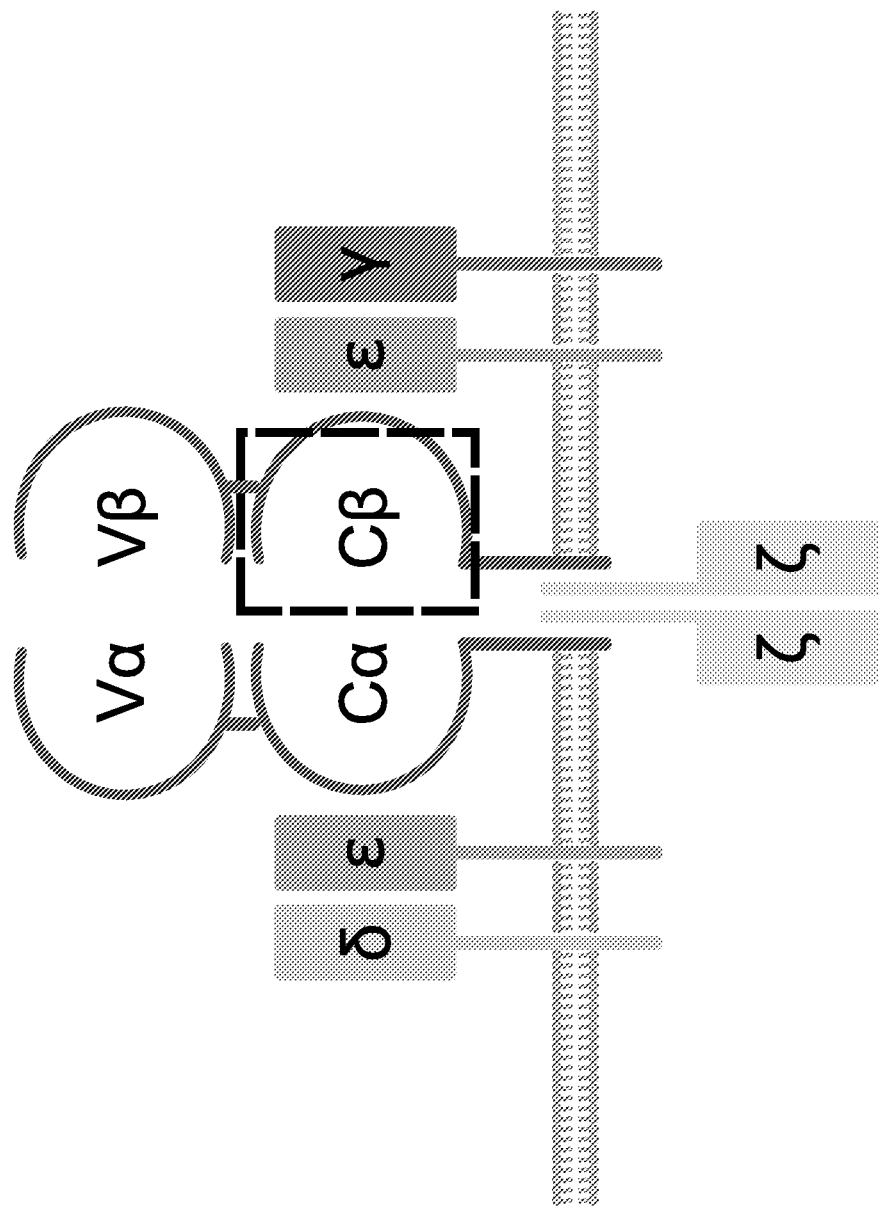
FIG. 1: A diagram of the αβ T-cell Receptor/CD3 Complex. The T-cell receptor is formed from 6 different protein chains which must assemble in the endoplasmic reticulum to be expressed on the cell surface. The four proteins of the CD3 complex (CD3ζ, CD3γ, CD3ε and CD3δ) sheath the T-cell Receptor (TCR). This TCR imbues the complex with specificity of a particular antigen and is composed of two chains: TCRα and TCRβ. Each TCR chain has a variable component distal to the membrane and a constant component proximal to the membrane. Nearly all T-cell lymphomas and many T-cell leukaemias express the TCR/CD3 complex.

The present inventors have developed anti-TRBC2 antibody using the intracellular portion of the TCR beta-2 chain. The antibody is specific for TRBC2 and can be used to stain for TRBC2 in fresh, frozen or fixed tissue samples. The antibody can be used to investigate the clonality of T-cell malignancies.

Thus, in a first aspect, the present invention provides an antibody which binds T-cell receptor constant region 2 (TRBC2) intracellular portion having the sequence shown as SEQ ID No. 1 (VKRKDSRG).

In a second aspect, the present invention provides a polyclonal antibody preparation which binds T-cell receptor constant region 2 (TRBC2) intracellular portion having the sequence shown as SEQ ID No. 1 (VKRKDSRG) and does not cross-react with T-cell receptor constant region 1 (TRBC1).

In a third aspect, the present invention provides a method for making a polyclonal antibody preparation according to the second aspect of the invention, which comprises the following steps:
(i) immunisation of an animal with a peptide comprising the sequence shown as SEQ ID No. 1 (VKRKDSRG);
(ii) isolation of antibodies from the serum of the immunised animal to give a polyclonal antibody preparation; and
(iii) depletion of any TRBC1-reactive antibodies using a peptide comprising the sequence shown as SEQ ID No. 2 (VKRKDF).

The same technology can be used to produce anti-TRBC1 antibodies using the intracellular portion of the TCR beta-1 chain. Thus, in a second embodiment of the first aspect of the invention, there is provided an antibody which binds T-cell receptor constant region 1 (TRBC1) intracellular portion having the sequence shown as SEQ ID No. 2 (VKRKDF).

In a second embodiment of the second aspect of the invention, there is provided a polyclonal antibody preparation which binds T-cell receptor constant region 1 (TRBC1) intracellular portion having the sequence shown as SEQ ID No. 2 (VKRKDF) and does not cross-react with T-cell receptor constant region 2 (TRBC2).

In a second embodiment of the third aspect of the invention there is provided a method for making a polyclonal antibody preparation according to the second embodiment of the second aspect of the invention, which comprises the following steps:
(i) immunisation of an animal with a peptide comprising the sequence shown as SEQ ID No. 2 (VKRKDF);
(ii) isolation of antibodies from the serum of the immunised animal to give a polyclonal antibody preparation; and
(iii) depletion of any TRBC2-reactive antibodies using a peptide comprising the sequence shown as SEQ ID No. 1 (VKRKDSRG).

In a fourth aspect, the present invention provides a method for investigating T-cell clonality of a T-cell malignancy in a subject which comprises the step of using an antibody according to the first aspect of the invention or a polyclonal antibody preparation according to the second aspect of the invention to establish whether malignant T cells from the subject express TRBC1 or TRBC2.

The method may comprise the step of investigating TRBC1/TRBC2 expression in a tissue sample from the subject.

The sample may be a formalin-fixed paraffin-embedded (FFPE) tissue sample.

TRBC1/TRBC2 expression may be investigated using a method such as immunohistochemistry.

In a fifth aspect, the present invention provides a method for treating a T-cell malignancy in a subject, which comprises the following steps:
a) investigating the clonality of the T-cell malignancy using a method according to the fourth aspect of the invention;
b) characterising the T-cell malignancy as either expressing TRBC1 or TRBC2; and
c) administering a TRBC1-specific therapeutic agent to a subject having a TRBC1-expressing T-cell malignancy; or
administering a TRBC2-specific therapeutic agent to a subject having a TRBC2-expressing T-cell malignancy.

The TRBC1-specific or TRBC2-specific therapeutic agent may, for example, be a therapeutic antibody, an antibody-drug conjugate, a bispecific T-cell engager, or a chimeric antigen receptor (CAR)-T cell composition.

The T-cell malignancy may be a T cell lymphoma or leukemia, such as one selected from: peripheral T-cell lymphoma, not otherwise specified (PTCL-NOS); angio-immunoblastic T-cell lymphoma (AITL); anaplastic large cell lymphoma (ALCL); enteropathy-associated T-cell lymphoma (EATL); hepatosplenic T-cell lymphoma (HSTL); extranodal NK/T-cell lymphoma nasal type; cutaneous T-cell lymphoma; primary cutaneous ALCL; T cell prolymphocytic leukaemia and T-cell acute lymphoblastic leukaemia (T-ALL).

DETAILED DESCRIPTION

TCR β Constant Region (TRBC)

The T-cell receptor (TCR) is expressed on the surface of T lymphocytes and is responsible for recognizing antigens bound to major histocompatibility complex (MHC) molecules. When the TCR engages with antigenic peptide and MHC (peptide/MHC), the T lymphocyte is activated through a series of biochemical events mediated by associated enzymes, co-receptors, specialized adaptor molecules, and activated or released transcription factors.

The TCR is a disulfide-linked membrane-anchored heterodimer normally consisting of the highly variable alpha (α) and beta (β) chains expressed as part of a complex with the invariant CD3 chain molecules. T-cells expressing this receptor are referred to as α:β (or αβ) T-cells (~95% total T-cells). A minority of T-cells express an alternate receptor, formed by variable gamma (γ) and delta (δ) chains, and are referred to as γδ T-cells (~5% total T cells).

Each α and β chain is composed of two extracellular domains: Variable (V) region and a Constant (C) region, both of Immunoglobulin superfamily (IgSF) domain forming antiparallel β-sheets. The constant region is proximal to the cell membrane, followed by a transmembrane region and a short cytoplasmic tail, while the variable region binds to the peptide/MHC complex (see FIG. 1). The constant region of the TCR consists of short connecting sequences in which a cysteine residue forms disulfide bonds, which forms a link between the two chains.

The variable domains of both the TCR α-chain and β-chain have three hypervariable or complementarity determining regions (CDRs). The variable region of the β-chain also has an additional area of hypervariability (HV4), however, this does not normally contact antigen and is therefore not considered a CDR.

The TCR also comprises up to five invariant chains γ,δ,ε (collectively termed CD3) and ζ. The CD3 and ζ subunits mediate TCR signalling through specific cytoplasmic domains which interact with second-messenger and adapter molecules following the recognition of the antigen by αβ or γδ. Cell-surface expression of the TCR complex is preceded by the pair-wise assembly of subunits in which both the transmembrane and extracellular domains of TCR α and β and CD3 γ and δ play a role.

TCRs are therefore commonly composed of the CD3 complex and the TCR α and β chains, which are in turn composed of variable and constant regions (FIG. 1).

Figure 2:
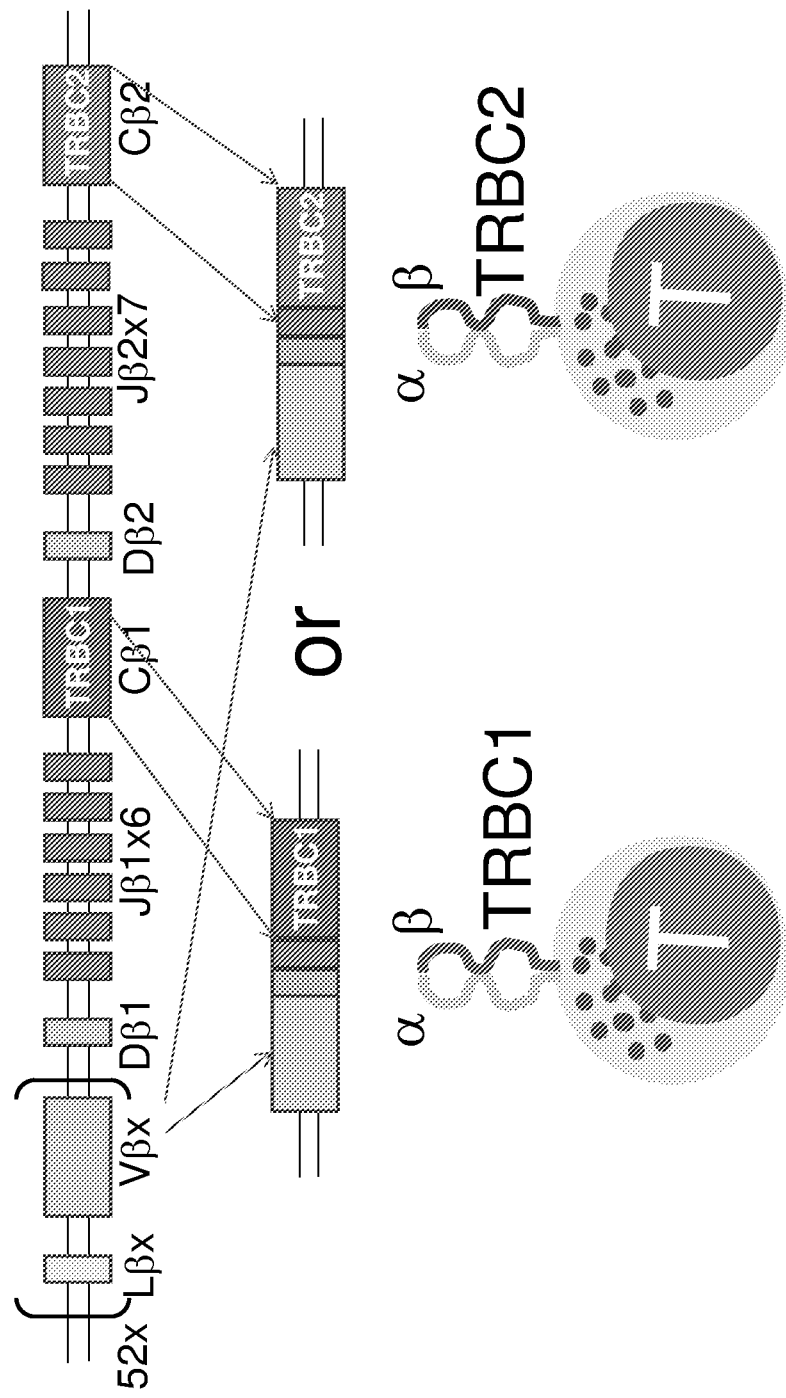
FIG. 2: The segregation of T-cell Receptor β-constant region (TRBC)-1 and TRBC2 during T-cell receptor rearrangement. Each TCR beta chain is formed from genomic recombination of a particular beta variable (V), diversity (D), joining (J) and constant (TRBC) regions. The human genome contains two very similar and functionally equivalent TRBC loci known as TRBC1 and TRBC2. During TCR gene re-arrangement, a J-region recombines with either TRBC1 or TRBC2. This rearrangement is permanent. T-cells express many copies of a single TCR on their surface, hence each T-cell will express a TCR whose β-chain constant region is coded for by either TRBC1 or TRBC2.

The locus (Chr7:q34) which supplies the TCR β-constant region (TRBC) has duplicated in evolutionary history to produce two almost identical and functionally equivalent genes: TRBC1 and TRBC2 (FIG. 2), which differ by only 4 amino acid in the extracellular domain (FIG. 3). Each TCR will comprise, in a mutually exclusive fashion, either TRBC1 or TRBC2 and as such, each αβ T-cell will express either TRBC1 or TRBC2, in a mutually exclusive manner.

The intracellular domain of TRBC1 and TRBC2 differ in the last three amino acids: TRBC2 has an eight amino-acid intracellular domain consisting of the sequence VKRKDSRG (SEQ ID No. 1) whereas TRBC1 has an intracellular domain consisting of the sequence VKRKDF (SEQ ID No. 2).

Antibody

The first aspect of the invention relates to an antibody which specifically binds either TRBC1 or TRBC2.

As used herein, "antibody" means a polypeptide having an antigen binding site which comprises at least one complementarity determining region CDR. The antibody may comprise 3 CDRs and have an antigen binding site which is equivalent to that of a domain antibody (dAb). The antibody may comprise 6 CDRs and have an antigen binding site which is equivalent to that of a classical antibody molecule. The remainder of the polypeptide may be any sequence which provides a suitable scaffold for the antigen binding site and displays it in an appropriate manner for it to bind the antigen. The antibody may be a whole immunoglobulin molecule or a part thereof such as a Fab, F(ab)'2, Fv, single chain Fv (ScFv) fragment or Nanobody. The antibody may be a bifunctional antibody. The antibody may be non-human, chimeric, humanised or fully human.

The antibody may therefore be any functional fragment which retains the antigen specificity of the full antibody.

The second aspect of the invention relates to a polyclonal antibody preparation which binds either TRBC1 or TRBC2.

Polyclonal antibodies are mixture of heterogeneous antibodies against a target antigen produced by different B cell clones in the body.

Polyclonal antibodies are produced by injecting an immunogen into an animal. After being injected with a specific antigen to elicit a primary immune response, the animal is given a secondary even tertiary immunization to produce higher titers of antibodies against the particular antigen. After immunization, polyclonal antibodies can be obtained straight from the serum (blood which has had clotting proteins and red blood cells removed) or purified to obtain a solution which is free from other serum proteins.

When an animal is immunised with the complete target antigen, the polyclonal antibody preparation will typically comprise antibodies which recognize and bind to many different epitopes of a the antigen.

The polyclonal antibody preparation of the present invention, however, recognises the intracellular portion of TRBC1 or TRBC2 so will bind either the sequence shown as SEQ ID No. 1 (VKRKDSRG) or the sequence shown as SEQ ID No. 2 (VKRKDF).

Monoclonal antibodies (mAbs) are generated by identical B cells which are clones from a single parent cell. This means that the monoclonal antibodies have monovalent affinity and only recognize the same epitope of an antigen.

Monoclonal antibodies may be made by immunising an animal as described above for a polyclonal antibody preparation, isolating B-lymphocytes from the animal's spleen and fusing the cells with a myeloma cell line, creating immortalized B cell-myeloma hybridomas. The hybridomas, which are able to grow continuously in culture while producing antibodies, are then screened for desired mAb.

The antibody of the first embodiment of the first aspect of the invention binds TRBC2 and does not cross-react with TRBC1.

A TRBC2 selective antibody may bind TRBC2 with an at least 2-fold, 4-fold, 5-fold, 7-fold or 10-fold greater affinity that TRBC1. The equilibrium dissociation constant ($K_D$) of binding to TRBC2 may be at least 2-fold, 4-fold, 5-fold, 7-fold or 10-fold higher than the KD value for binding TRBC1.

The antibody of the second embodiment of the first aspect of the invention binds TRBC1 and does not cross-react with TRBC2. A TRBC1 selective antibody may bind TRBC1 with an at least 2-fold, 4-fold, 5-fold, 7-fold or 10-fold greater affinity that TRBC2. The equilibrium dissociation constant (KD) of binding to TRBC1 may be at least 2-fold, 4-fold, 5-fold, 7-fold or 10-fold higher than the KD value for binding TRBC2.

The binding of an antibody or polyclonal antibody preparation to TRBC1 or TRBC2 may be investigated by methods such as ELISA. For example, an ELISA may be carried out with the peptides VKRKDSRG (SEQ ID No. 1) from TRBC2 and VKRKDF (SEQ ID No.2) from TRBC1. A TRBC2-specific polyclonal antibody preparation may show at least 2-fold, 4-fold, 5-fold, 7-fold or 10-fold higher binding to SEQ ID No. 1 than SEQ ID No. 2. A TRBC1-specific polyclonal antibody preparation may show at least 2-fold, 4-fold, 5-fold, 7-fold or 10-fold higher binding to SEQ ID No. 2 than SEQ ID No. 1.

The EC50 of an antibody or plyclonal antibody preparation is the concentration of antibody which induces a response halfway between the baseline and maximum. Example 1 herein describes the generation of an anti-TRBC2 polyclonal antibody which has an EC50 to the TRBC1 peptide (SEQ ID No. 2) of 88 ug/ml and an EC50 to the TRBC2 peptide (SEQ ID No. 1) of 54 ng/ml. A TRBC1- or TRBC2-specific polyclonal antibody preparation may show at least 10-fold, 100-fold, 500-fold or 1000-fold differential in EC50 between SEQ ID No. 1 and SEQ ID No. 2 peptides.

METHOD FOR MAKING POLYCLONAL ANTIBODY PREPARATION

The present invention also provides a method for making an antibody according to the first aspect of the invention or a polyclonal antibody preparation according to the second aspect of the invention.

A TRBC2-specific polyclonal antibody preparation may be made by a method which comprises the following steps:
(i) immunisation of an animal with a peptide comprising the sequence shown as SEQ ID No. 1 (VKRKDSRG); and
(ii) isolation of antibodies from the serum of the immunised animal to give a polyclonal antibody preparation.

Immunoglobulin may be purified from serum by techniques known in the art, such as using Protein A.

The polyclonal antibody preparation may be purified to remove any TRBC1-reactive antibodies. TRBC1-reactive antibodies may be depleted using a TRBC-1 derived peptide, for example a peptide comprising the sequence shown as SEQ ID No. 2 (VKRKDF). The depletion step may be carried out using, for example, TRBC-1 peptide-coated agarose beads.

A TRBC1-specific polyclonal antibody preparation may be made by a method which comprises the following steps:
(i) immunisation of an animal with a peptide comprising the sequence shown as SEQ ID No. 2 (VKRKDF); and
(ii) isolation of antibodies from the serum of the immunised animal to give a polyclonal antibody preparation.

The polyclonal antibody preparation may be purified to remove any TRBC2-reactive antibodies. TRBC2-reactive antibodies may be depleted using a TRBC-1 derived peptide, for example a peptide comprising the sequence shown as SEQ ID No. 1 (VKRKDSRG).

METHOD FOR DETERMINING T-CELL CLONALITY

The present invention provides a method for investigating T-cell clonality of a T-cell malignancy in a subject by using an antibody or a polyclonal antibody preparation of the invention to establish whether malignant T cells from the subject express TRBC1 or TRBC2. The method may involve determining the proportion of T-cells in a sample from a subject which are either TRBC1 or TRBC2 positive.

T-cell lymphomas involve the clonal expansion of individual malignant T-cells. As such the presence of a T-cell lymphoma in a subject may be identified by determining the proportion of either TRBC1 or TRBC2 T-cells in a sample derived from a patient.

The sample may be a peripheral blood sample, a lymph sample or a sample taken directly from a tumour e.g. a biopsy sample.

The proportion of total T-cells which are TRBC1 or TRBC2 positive which indicates the presence of a T-cell lymphoma or leukaemia may be, for example 80, 85, 90, 95, 98 or 99% of a total population of cells.

The method may involve determining infiltration by a distinct population of T-cells in a biopsy or a sample, in which case the presence of a T-cell lymphoma or leukaemia may be indicated where 80, 85, 90, 95, 98 or 99% of a total population of T cells in the sample are either TRBC1 or TRBC2.

The total T-cells in a sample may identified by determining the number of cells in the sample which express CD3, CD4, CD8 and/or CD45. A combination of these markers may also be used.

The proportion of total T cells in a sample which express either TRBC1 or TRBC2 may be determined using methods which are known in the art, for example flow cytometry, immunohistochemistry or fluorescent microscopy.

METHOD OF TREATMENT

The present invention provides a method for treating a T-cell malignancy in a subject, which comprises the step of administering a TRBC1-specific therapeutic agent to a subject who has been established to have a TRBC1-expressing T-cell malignancy; or administering a TRBC2-specific therapeutic agent to a subject who has been established to have a TRBC2-expressing T-cell malignancy.

Administration of a TRBC1-specific therapeutic agent may cause TRBC1-expressing healthy and malignant T cells to be depleted in the subject, but TRBC2-expressing healthy cells to be spared.

Administration of a TRBC2-specific therapeutic agent may cause TRBC2-expressing healthy and malignant T cells to be depleted in the subject, but TRBC1-expressing healthy cells to be spared.

The TRBC1-specific or TRBC2-specific therapeutic agent may, for example be a therapeutic antibody, an antibody-drug conjugate, a bispecific T-cell engager, or a chimeric antigen receptor (CAR)-T cell composition.

Therapeutic Antibody

The therapeutic agent used in the method of the present invention may be a TRBC1- or TRBC2-specific depleting monoclonal antibody (mAb) or a functional fragment thereof.

The term 'depleting antibody' is used in the conventional sense to relate to an antibody which binds to an antigen present on a target T-cell and mediates death of the target T-cell. The administration of a depleting antibody to a subject therefore results in a reduction/decrease in the number of cells within the subject which express the target antigen.

AN anti-TRBC1 therapeutic agent for use in the method of the present invention may comprise an antibody or a functional fragment thereof having a variable heavy chain (VH) and a variable light chain (VL) which comprises the following complementarity determining regions (CDRs):

```
VH CDR1:
                                        (SEQ ID No. 3)
GYTFTGY;

VH CDR2:
                                        (SEQ ID No. 4)
NPYNDD;

VH CDR3:
                                        (SEQ ID No. 5)
GAGYNFDGAYRFFDF;

VL CDR1:
                                        (SEQ ID No. 6)
RSSQRLVHSNGNTYLH;

VL CDR2:
                                        (SEQ ID No. 7)
RVSNRFP;
and

VL CDR3:
                                        (SEQ ID No. 8)
SQSTHVPYT.
```

Conjugates

The therapeutic agent used in the method of the present invention may be an antibody-drug conjugate, where a TRBC1 or TRBC2-specific antibody is conjugated to a drug such as a chemotherapeutic entity.

A chemotherapeutic entity as used herein refers to an entity which is destructive to a cell, that is the entity reduces the viability of the cell. The chemotherapeutic entity may be a cytotoxic drug. A chemotherapeutic agent contemplated includes, without limitation, alkylating agents, nitrosoureas, ethylenimines/methylmelamine, alkyl sulfonates, antimetabolites, pyrimidine analogs, epipodophylotoxins, enzymes such as L-asparaginase; biological response modifiers such as IFNα, IL-2, G-CSF and GM-CSF; platinium coordination complexes such as cisplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

A TRBC selective agent conjugated to a chemotherapeutic entity enables the targeted delivery of the chemotherapeutic entity to cells which express either TRBC1 or TRBC2.

The "antibody" part of the drug conjugate may be an antibody fragment, such as an scFv. An anti-TRBC1 drug conjugate may comprise a VH and VL having CDRs with SEQ ID No.s 3 to 8 as defined above.

Bi-Specific T-Cell Engagers

A wide variety of molecules have been developed which are based on the basic concept of having two antibody-like binding domains.

Bispecific T-cell engaging molecules are a class of bispecific antibody-type molecules that have been developed, primarily for the use as anti-cancer drugs. They direct a host's immune system, more specifically the T cells' cytotoxic activity, against a target cell, such as a cancer cell. In these molecules, one binding domain binds to a T cell via the CD3 receptor, and the other to a target cells such as a tumor cell (via a tumor specific molecule). Since the bispecific molecule binds both the target cell and the T cell, it brings the target cell into proximity with the T cell, so that the T cell can exert its effect, for example, a cytotoxic effect on a cancer cell. The formation of the T cell:bispecific Ab:cancer cell complex induces signaling in the T cell leading to, for example, the release of cytotoxic mediators. Ideally, the agent only induces the desired signaling in the presence of the target cell, leading to selective killing.

Bispecific T-cell engaging molecules have been developed in a number of different formats, but one of the most common is a fusion consisting of two single-chain variable fragments (scFvs) of different antibodies. These are sometimes known as BiTEs (Bi-specific T-cell Engagers).

The therapeutic agent used in the method of the present invention may be a bi-specific molecule which selectively recognises TRBC1 or TRBC2 and is capable of activating a T cell. For example the agent may be a BiTE. The agent used in the method may comprise:

(i) a first domain which binds either TRBC1 or TRBC2; and
(ii) a second domain capable of activating a T cell.

The bi-specific molecule may comprise a signal peptide to aid in its production. The signal peptide may cause the bi-specific molecule to be secreted by a host cell, such that the bi-specific molecule can be harvested from the host cell supernatant.

The signal peptide may be at the amino terminus of the molecule. The bi-specific molecule may have the general formula: Signal peptide—first domain—second domain.

The bi-specific molecule may comprise a spacer sequence to connect the first domain with the second domain and spatially separate the two domains.

The spacer sequence may, for example, comprise an IgG1 hinge or a CD8 stalk. The linker may alternatively comprise an alternative linker sequence which has similar length and/or domain spacing properties as an IgG1 hinge or a CD8 stalk.

The first domain of an anti-TRBC1 bi-specific molecule may comprise comprise a VH and VL having CDRs with SEQ ID No.s 3 to 8 as defined above.

Chimeric Antigen Receptor (CAR)

Chimeric antigen receptors (CARs), also known as chimeric T-cell receptors, artificial T-cell receptors and chimeric immunoreceptors, are engineered receptors, which graft an arbitrary specificity onto an immune effector cell. In a classical CAR, the specificity of a monoclonal antibody is grafted on to a T-cell. CAR-encoding nucleic acids may be transferred to T-cells using, for example, retroviral vectors. In this way, a large number of cancer-specific T-cells can be generated for adoptive cell transfer. Phase I clinical studies of this approach show efficacy.

The target-antigen binding domain of a CAR is commonly fused via a spacer and transmembrane domain to an endodomain, which comprises or associates with an intracellular T-cell signalling domain. When the CAR binds the target-antigen, this results in the transmission of an activating signal to the T-cell it is expressed on.

The therapeutic agent used in the method of the present invention may be a cell such as a T-cell which expresses a CAR that selectively recognises TRBC1 or TRBC2.

The endodomain is the portion of the CAR involved in signal-transmission. The endodomain either comprises or associates with an intracellular T-cell signalling domain. After antigen recognition, receptors cluster and a signal is transmitted to the cell. The most commonly used T-cell signalling component is that of CD3-zeta which contains 3 ITAMs. This transmits an activation signal to the T-cell after antigen is bound. CD3-zeta may not provide a fully competent activation signal and additional co-stimulatory signaling may be needed. For example, chimeric CD28 and OX40 or 4-1BB can be used with CD3-Zeta to transmit a proliferative/survival signal, or all three can be used together.

The CAR may comprise a spacer sequence to connect the TRBC-binding domain with the transmembrane domain and spatially separate the TRBC-binding domain from the endodomain. A flexible spacer allows to the TRBC-binding domain to orient in different directions to enable TRBC binding.

The spacer sequence may, for example, comprise an IgG1 hinge or a CD8 stalk.

The antigen-binding domain of an anti-TRBC1-CAR may comprise a VH and VL having CDRs with SEQ ID Nos 3 to 8 as defined above.

T-Cell Lymphoma and/or Leukaemia

The invention provides a method for treating a T cell malignancy by administering a TRBC1-specific or a TRBC2-specific agent. The agent may be administered to a subject having an existing T-cell malignancy in order to lessen, reduce or improve at least one symptom associated with the disease and/or to slow down, reduce or block the progression of the disease.

The method of the present invention may be used for the treatment of any lymphoma and/or leukaemia associated with the clonal expansion of a cell expressing a T-cell receptor (TCR) comprising a β constant region. As such the present invention relates to a method for treating a disease which involves malignant T cells which express a TCR comprising a TRBC.

The method of the present invention may be used to treat a T-cell lymphoma in which the malignant T-cell expresses a TCR comprising a TRBC. 'Lymphoma' is used herein according to its standard meaning to refer to a cancer which typically develops in the lymph nodes, but may also affect the spleen, bone marrow, blood and other organs. Lymphoma typically presents as a solid tumour of lymphoid cells. The primary symptom associated with lymphoma is lymphadenopathy, although secondary (B) symptoms can include fever, night sweats, weight loss, loss of appetite, fatigue, respiratory distress and itching.

The method of the present invention may be used to treat a T-cell leukaemia in which the malignant T-cell expresses a TCR comprising a TRBC. 'Leukaemia' is used herein according to its standard meaning to refer to a cancer of the blood or bone marrow.

The following is an illustrative, non-exhaustive list of diseases which may be treated by the method of the present invention.

Peripheral T-Cell Lymphoma

Peripheral T-cell lymphomas are relatively uncommon lymphomas and account fewer than 10% of all non-Hodgkin lymphomas (NHL). However, they are associated with an aggressive clinical course and the causes and precise cellular origins of most T-cell lymphomas are still not well defined.

Lymphoma usually first presents as swelling in the neck, underarm or groin. Additional swelling may occur where other lymph nodes are located such as in the spleen. In general, enlarged lymph nodes can encroach on the space of blood vessels, nerves, or the stomach, leading to swollen arms and legs, to tingling and numbness, or to feelings of being full, respectively. Lymphoma symptoms also include nonspecific symptoms such as fever, chills, unexplained weight loss, night sweats, lethargy, and itching.

The WHO classification utilizes morphologic and immunophenotypic features in conjunction with clinical aspects and in some instances genetics to delineate a prognostically and therapeutically meaningful categorization for peripheral T-cell lymphomas (Swerdlow et al; WHO classification of tumours of haematopoietic and lymphoid tissues. 4th ed.; Lyon: IARC Press; 2008). The anatomic localization of neoplastic T-cells parallels in part their proposed normal cellular counterparts and functions and as such T-cell lymphomas are associated with lymph nodes and peripheral blood. This approach allows for better understanding of some of the manifestations of the T-cell lymphomas, including their cellular distribution, some aspects of morphology and even associated clinical findings.

The most common of the T-cell lymphomas is peripheral T-cell lymphoma, not otherwise specified (PTCL-NOS) comprising 25% overall, followed by angioimmunoblastic T-cell lymphoma (AITL) (18.5%)

Peripheral T-Cell Lymphoma, not Otherwise Specified (PTCL-NOS)

PTCL-NOS comprises over 25% of all peripheral T-cell lymphomas and NK/T-cell lymphomas and is the most common subtype. It is determined by a diagnosis of exclusion, not corresponding to any of the specific mature T-cell lymphoma entities listed in the current WHO 2008. As such it is analogous to diffuse large B-cell lymphoma, not otherwise specified (DLBCL-NOS).

Most patients are adults with a median age of 60 and a male to female ratio 2:1. The majority of cases are nodal in origin, however, extranodal presentations occur in approximately 13% of patients and most commonly involve skin and gastrointestinal tract.

The cytologic spectrum is very broad, ranging from polymorphous to monomorphous. Three morphologically defined variants have been described, including lymphoepithelioid (Lennert) variant, T-zone variant and follicular variant. The lymphoepithelioid variant of PTCL contains abundant background epithelioid histiocytes and is commonly positive for CD8. It has been associated with a better prognosis. The follicular variant of PTCL-NOS is emerging as a potentially distinct clinicopathologic entity.

The majority of PTCL-NOS have a mature T-cell phenotype and most cases are CD4-positive. 75% of cases show variable loss of at least one pan T-cell marker (CD3, CD2, CD5 or CD7), with CD7 and CD5 being most often downregulated. CD30 and rarely CD15 can be expressed, with CD15 being an adverse prognostic feature. CD56 expression, although uncommon, also has negative prognostic impact.

Additional adverse pathologic prognostic factors include a proliferation rate greater than 25% based on KI-67 expression, and presence of more than 70% transformed cells.

Immunophenotypic analysis of these lymphomas has offered little insight into their biology.

Angioimmunoblastic T-Cell Lymphoma (AITL)

AITL is a systemic disease characterized by a polymorphous infiltrate involving lymph nodes, prominent high endothelial venules (HEV) and peri-vascular expansion of follicular dendritic cell (FDC) meshworks. AITL is considered as a de-novo T-cell lymphoma derived from αβ T-cells of follicular helper type (TFH), normally found in the germinal centres.

AITL is the second most common entity among peripheral T-cell lymphoma and NK/T-cell lymphomas, comprising about 18.5% of cases. It occurs in middle aged to elderly adults, with a median age of 65 years old, and an approximately equal incidence in males and females. Clinically, patients usually have advanced stage disease, with generalized lymphadenopathy, hepatosplenomegaly and prominent constitutional symptoms. Skin rash with associated pruritus is commonly present. There is often polyclonal hypergammaglobulinemia, associated with autoimmune phenomena.

Three different morphologic patterns are described in AITL. The early lesion of AITL (Pattern I) usually shows preserved architecture with characteristic hyperplastic follicles. The neoplastic proliferation is localized to the periphery of the follicles. In Pattern II the nodal architecture is partially effaced with retention of few regressed follicles. The subcapsular sinuses are preserved and even dilated. The paracortex contains arborizing HEV and there is a proliferation of FDC beyond the B-cell follicle. The neoplastic cells are small to medium in size, with minimal cytologic atypia. They often have clear to pale cytoplasm, and may show distincT-cell membranes. A polymorphous inflammatory background is usually evident.

Although AITL is a T-cell malignancy, there is a characteristic expansion of B-cells and plasma cells, which likely reflects the function of the neoplastic cells as TFH cells. Both EBV-positive and EBV-negative B-cells are present. Occasionally, the atypical B-cells may resemble Hodgkin/Reed-Sternberg-like cells morphologically and immunophenotypically, sometimes leading to a diagnostic confusion with that entity. The B-cell proliferation in AITL may be extensive and some patients develop secondary EBV-positive diffuse large B-cell lymphomas (DLBCL) or—more rarely—EBV-negative B-cell tumors, often with plasmacytic differentiation.

The neoplastic CD4-positive T-cells of AITL show strong expression of CD10 and CD279 (PD-1) and are positive for CXCL13. CXCL13 leads to an increased B-cell recruitment to lymph nodes via adherence to the HEV, B-cell activation, plasmacytic differentiation and expansion of the FDC meshworks, all contributing to the morphologic and clinical features of AITL. Intense PD-1-expression in the perifollicular tumor cells is particularly helpful in distinguishing AITL Pattern I from reactive follicular and paracortical hyperplasia.

The follicular variant of PTCL-NOS is another entity with a TFH phenotype. In contradistinction to AITL, it does not have prominent HEV or extra-follicular expansion of FDC meshworks. The neoplastic cells may form intrafollicular aggregates, mimicking B-cell follicular lymphoma, but also can have interfollicular growth pattern or involve expanded mantle zones. Clinically, the follicular variant of PTCL-NOS is distinct from AITL as patients more often present with early stage disease with partial lymph node involvement and may lack the constitutional symptoms associated with AITL.

Anaplastic Large Cell Lymphoma (ALCL)

ALCL may be subdivided as ALCL-'anaplastic lymphoma kinase' (ALK)+or ALCL-ALK−.

ALCL-ALK+ is one of the best-defined entities within the peripheral T-cell lymphomas, with characteristic "hallmark cells" bearing horseshoe-shaped nuclei and expressing ALK and CD30. It accounts for about 7% of all peripheral T-cell and NK-cell lymphomas and is most common in the first three decades of life. Patients often present with lymphadenopathy, but the involvement of extranodal sites (skin, bone, soft tissues, lung, liver) and B symptoms is common.

ALCL, ALK+ shows a wide morphologic spectrum, with 5 different patterns described, but all variants contain some hallmark cells. Hallmark cells have eccentric horseshoe- or kidney-shaped nuclei, and a prominent perinuclear eosinophilic Golgi region. The tumour cells grow in a cohesive pattern with predilection for sinus involvement. Smaller tumour cells predominate in the small cell variant, and in the lymphohistiocytic variant abundant histiocytes mask the presence of tumour cells, many of which are small.

By definition, all cases show ALK and CD30positivity, with expression usually weaker in the smaller tumour cells. There is often loss of pan-T-cell markers, with 75% of cases lacking surface expression of CD3.

ALK expression is a result of a characteristic recurrent genetic alteration consisting of a rearrangement of ALK gene on chromosome 2p23 to one of the many partner genes, resulting in an expression of chimeric protein. The most common partner gene, occurring in 75% of cases, is Nucleophosmin (NPM1) on chromosome 5q35, resulting in t(2;5)(p23;q35). The cellular distribution of ALK in different translocation variants may vary depending on the partner gene.

ALCL-ALK− is included as a provisional category in the 2008 WHO classification. It is defined as a CD30 positive T-cell lymphoma that is morphologically indistinguishable from ALCL-ALK+ with a cohesive growth pattern and presence of hallmark cells, but lacking ALK protein expression.

Patients are usually adults between the ages of 40 and 65, in contrast to ALCL-ALK+, which is more common in children and young adults. ALCL-ALK− can involve both lymph nodes and extranodal tissues, although the latter is seen less commonly than in ALCL-ALK+. Most cases of ALCL-ALK− demonstrate effacement of lymph node architecture by sheets of cohesive neoplastic cells with typical "hallmark" features. In contrast to the ALCL-ALK+, the small cell morphologic variant is not recognized.

Unlike its ALK+ counterpart, ALCL-ALK− shows a greater preservation of surface T-cell marker expression, while the expression of cytotoxic markers and epithelial membrane antigen (EMA) is less likely. Gene expression signatures and recurrent chromosomal imbalances are different in ALCL-ALK− and ALCL-ALK+, confirming that they are distinct entities at a molecular and genetic level.

ALCL-ALK− is clinically distinct from both ALCL-ALK+ and PTCL-NOS, with significant differences in prognosis among these three different entities. The 5 year overall survival of ALCL-ALK− is reported as 49% which is not as good as that of ALCL-ALK+ (at 70%), but at the same time it is significantly better than that of PTCL-NOS (32%).

Enteropathy-Associated T-Cell Lymphoma (EATL)

EATL is an aggressive neoplasm which thought to be derived from the intraepithelial T-cells of the intestine. Two morphologically, immunohistochemically and genetically distinct types of EATL are recognized in the 2008 WHO classification: Type I (representing the majority of EATL) and Type II (comprising 10-20% of cases).

Type I EATL is usually associated with overt or clinically silent gluten-sensitive enteropathy, and is more often seen in patients of Northern European extraction due to high prevalence of celiac disease in this population.

Most commonly, the lesions of EATL are found in the jejunum or ileum (90% of cases), with rare presentations in duodenum, colon, stomach, or areas outside of the gastrointestinal tract. The intestinal lesions are usually multifocal with mucosal ulceration. Clinical course of EATL is aggressive with most patients dying of disease or complications of disease within 1 year.

The cytological spectrum of EATL type I is broad, and some cases may contain anaplastic cells. There is a polymorphous inflammatory background, which may obscure the neoplastic component in some cases. The intestinal mucosa in regions adjacent to the tumour often shows features of celiac disease with blunting of the villi and increased numbers of intraepithelial lymphocytes (IEL), which may represent lesional precursor cells.

By immunohistochemistry, the neoplastic cells are often CD8+CD4−CD8−CD7+CD5−CD56−βF1+, and contain cytotoxic granule-associated proteins (T1A-1, granzyme B, perforin). CD30 is partially expressed in almost all cases. CD103, which is a mucosal horning receptor, can be expressed in EATL.

Type II EATL, also referred to as monomorphic CD56+ intestinal T-cell lymphoma, is defined as an intestinal tumour composed of small- to medium-sized monomorphic T-cells that express both CD8 and CD56. There is often a lateral spread of tumour within the mucosa, and absence of an inflammatory background. The majority of cases express the γδ TCR, however there are cases associated with the αβ TCR.

Type II EATL has a more world-wide distribution than Type I EATL and is often seen in Asians or Hispanic populations, in whom celiac disease is rare. In individuals of European descent EATL, II represents about 20% of intestinal T-cell lymphomas, with a history of celiac disease in at least a subset of cases. The clinical course is aggressive.

Hepatosplenic T-Cell Lymphoma (HSTL)

HSTL is an aggressive systemic neoplasm generally derived from γδ cytotoxic T-cells of the innate immune system, however, it may also be derived from αβT-cells in rare cases. It is one of the rarest T-cell lymphomas, and typically affects adolescents and young adults (median age, 35 years) with a strong male predominance.

Extranodal NK/T-Cell Lymphoma Nasal Type

Extranodal NK/T-cell lymphoma, nasal type, is an aggressive disease, often with destructive midline lesions and necrosis. Most cases are of NK-cell derivation, but some cases are derived from cytotoxic T-cells. It is universally associated with Epstein-Barr Virus (EBV).

Cutaneous T-Cell Lymphoma

The method of the present invention may also be used to treat cutaneous T-cell lymphoma.

Cutaneous T-cell lymphoma (CTCL) is characterised by migration of malignant T-cells to the skin, which causes various lesions to appear. These lesions change shape as the disease progresses, typically beginning as what appears to be a rash and eventually forming plaques and tumours before metastasizing to other parts of the body.

Cutaneous T-cell lymphomas include those mentioned in the following illustrative, non-exhaustive list; mycosis fungoides, pagetoid reticulosis, Sézary syndrome, granulomatous slack skin, lymphomatoid papulosis, pityriasis lichenoides chronica, CD30+ cutaneous T-cell lymphoma, secondary cutaneous CD30+ large cell lymphoma, non-mycosis fungoides CD30− cutaneous large T-cell lymphoma, pleomorphic T-cell lymphoma, Lennert lymphoma, subcutaneous T-cell lymphoma and angiocentric lymphoma.

The signs and symptoms of CTCL vary depending on the specific disease, of which the two most common types are mycosis fungoides and Sézary syndrome. Classic mycosis fungoides is divided into three stages:

Patch (atrophic or nonatrophic): Nonspecific dermatitis, patches on lower trunk and buttocks; minimal/absent pruritus;

Plaque: Intensely pruritic plaques, lymphadenopathy; and

Tumor: Prone to ulceration

Sézary syndrome is defined by erythroderma and leukemia. Signs and symptoms include edematous skin, lymphadenopathy, palmar and/or plantar hyperkeratosis, alopecia, nail dystrophy, ectropion and hepatosplenomegaly.

Of all primary cutaneous lymphomas, 65% are of the T-cell type. The most common immunophenotype is CD4 positive. There is no common pathophysiology for these diseases, as the term cutaneous T-cell lymphoma encompasses a wide variety of disorders.

The primary etiologic mechanisms for the development of cutaneous T-cell lymphoma (ie, mycosis fungoides) have not been elucidated. Mycosis fungoides may be preceded by a T-cell-mediated chronic inflammatory skin disease, which may occasionally progress to a fatal lymphoma.

Primary Cutaneous ALCL (C-ALCL)

C-ALCL is often indistinguishable from ALC-ALK− by morphology. It is defined as a cutaneous tumour of large cells with anaplastic, pleomorphic or immunoblastic morphology with more than 75% of cells expressing CD30. Together with lymphomatoid papulosis (LyP), C-ALCL belongs to the spectrum of primary cutaneous CD30-positive T-cell lymphoproliferative disorders, which as a group comprise the second most common group of cutaneous T-cell lymphoproliferations after mycosis fungoides.

The immunohistochemical staining profile is quite similar to ALCL-ALK−, with a greater proportion of cases staining positive for cytotoxic markers. At least 75% of the tumour cells should be positive for CD30. CD15 may also be expressed, and when lymph node involvement occurs, the differential with classical Hodgkin lymphoma can be difficult. Rare cases of ALCL-ALK+ may present with localized cutaneous lesions, and may resernble C-ALCL.

T-Cell Acute Lymphoblastic Leukaemia

T-cell acute lymphoblastic leukaemia (T-ALL) accounts for about 15% and 25% of ALL in paediatric and adult cohorts respectively. Patients usually have high white blood cell counts and may present with organomegaly, particularly mediastinal enlargement and CNS involvement.

The method of the present invention may be used to treat T-ALL which is associated with a malignant T cell which expresses a TCR comprising a TRBC.

T-Cell Prolymphocytic Leukaemia

T-cell-prolymphocytic leukemia (T-PLL) is a mature T-cell leukaemia with aggressive behaviour and predilection for blood, bone marrow, lymph nodes, liver, spleen, and skin involvement. T-PLL primarily affects adults over the age of 30. Other names include T-cell chronic lymphocytic leukaemia, "knobby" type of T-cell leukaemia, and T-prolymphocytic leukaemia/T-cell lymphocytic leukaemia.

In the peripheral blood, T-PLL consists of medium-sized lymphocytes with single nucleoli and basophilic cytoplasm with occasional blebs or projections. The nuclei are usually round to oval in shape, with occasional patients having cells with a more irregular nuclear outline that is similar to the cerebriform nuclear shape seen in Sézary syndrome. A small cell variant comprises 20% of all T-PLL cases, and the Sézary cell-like (cerebriform) variant is seen in 5% of cases.

T-PLL has the immunophenotype of a mature (post-thymic) T-lymphocyte, and the neoplastic cells are typically positive for pan-T antigens CD2, CD3, and CD7 and negative for TdT and CD1a. The immunophenotype CD4+/CD8− is present in 60% of cases, the CD4+/CD8+ immunophenotype is present in 25%, and the CD4−/CD8+ immunophenotype is present in 15% of cases

EXAMPLES

Example 1—Generation of Anti-TRBC-2 Antibody

Figure 5:
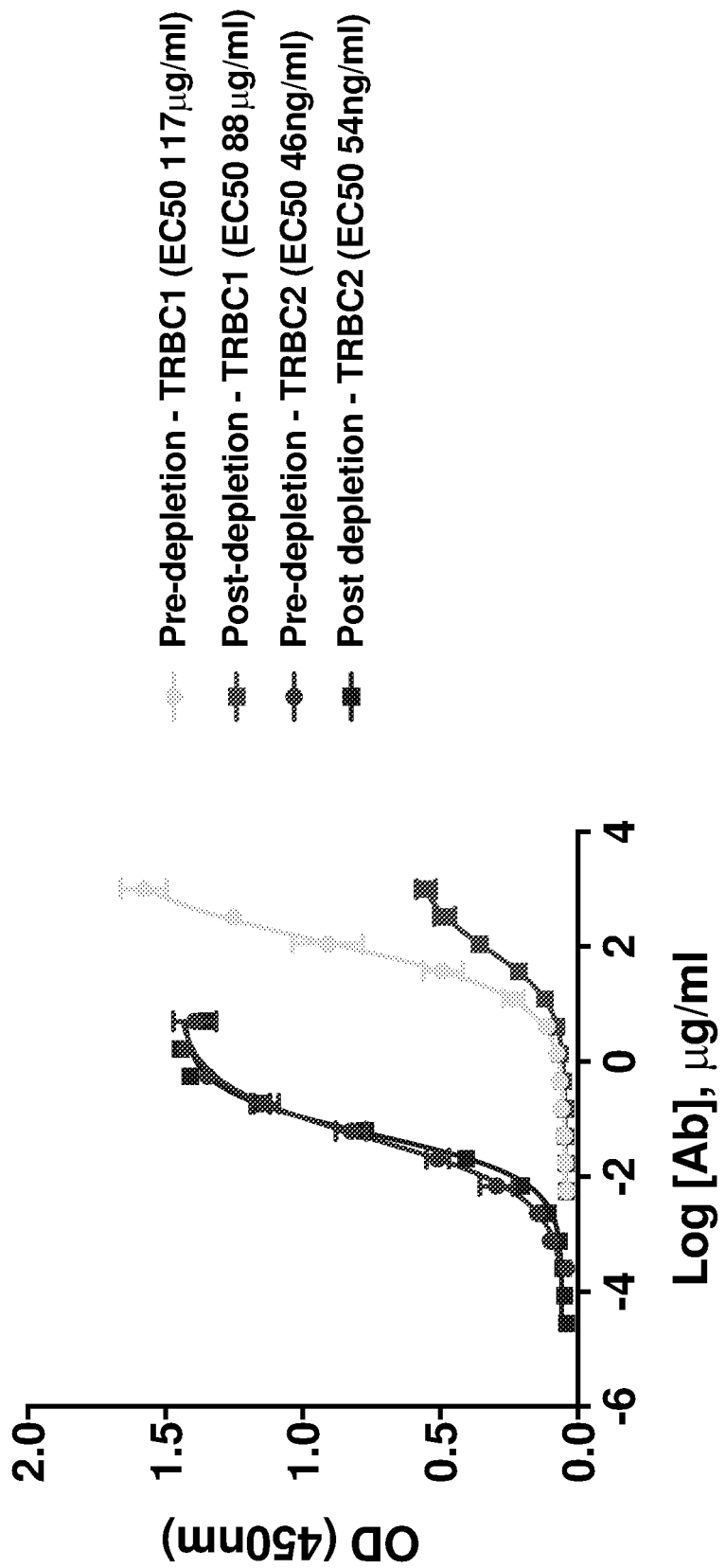
FIG. 5: TRBC1 and TRBC2 specificity of polyclonal antibody preparation before and after depletion step with TRBC1 peptide.

To generate anti-TRBC2 antibody, New Zealand rabbits were immunised with a peptide comprising the intracellular portion of the TCR beta-2 chain (VKRKDSRG) using the protocol illustrated schematically in FIG. 4. Protein A-purified immunoglobulin from the sera of immunised rabbits was tested for reactivity to TRBC1 (VKRKDF) and TRBC2 peptides by ELISA. Strong TRBC2-specificity with limited TRBC1 binding was seen. Following this, immunoglobulin was depleted of residual TRBC1 reactivity by depletion on TRBC1 peptide-coated agarose beads. Following this, no reactivity to TRBC1 peptide could be detected by ELISA (FIG. 5).

Example 2—Staining of T-Cell Lines

Fresh frozen and FFPE samples of pelleted TRBC1 and TRBC2 cell lines were then stained with the novel, polyclonal anti-TRBC2 antibody. It was confirmed that anti-TRBC2 antibody stained the TRBC2 cell line: HPB-ALL, but not the TRBC1 cell lines: Jurkat and H9. The antibody performed equivalently in fresh or FFPE preparations. In a range of normal tissues, including tonsil, spleen and others, a staining pattern restricted to only a proportion of T-cells was seen.

Example 3—Staining of T-Cell Malignancies and Verification by Analysis of VDJ Rearrangement Paired FFPE and frozen samples of several TCR+ T-cell malignancies were obtained and stained for TRBC1 (frozen only) and TRBC2. In addition, DNA was extracted from these tissues and PCR was performed for TCR beta VDJ rearrangement using standard BIOMED protocols. Clonal proliferations were identified by heteroduplex gel analysis and capillary electrophoresis sequencing was performed on dominant bands. In addition, pooled PCR products were subjected to massively parallel sequencing to quantify clone frequency and to confirm VDJ identity. Mutual exclusivity was demonstrated between samples staining positive for TRBC1 and TRBC2, and concordance between TRBC1/2 status identified by sequencing, NGS and antibody-based methods.

Example 4—TRBC2 Antibody Staining of Fixed Samples of T-Cell and Non-T Cell Tumours In a number of TCR+ malignancies, non-T-cell haematological tumours and reactive lymphoproliferations where only FFPE material was available, the anti-TRBC2 antibody was used to evaluate TRBC2 expression. FFPE samples of T-cell and non-T cell tumours across a range of histologies were stained with anti-TRBC2. It was demonstrated that in non-T cell tumours, a limited pattern of staining was seen, restricted to a proportion of infiltrating normal T-cells only. T-cell tumours, by contrast, were uniformly TRBC2-negative or positive. The data are summarised in Table 1 below. 18/29 (62%) of tumours were TRBC2-positive.

TABLE 1

| Lymphoma/Leukaemia entity | | CD3 + (%) | TRBC2 + (%) |
|---|---|---|---|
| B-cell lymphoma | CLL | 0/6 | 0/6 |
| | Mantle Cell | 0/6 | 0/6 |
| | Follicular Centre | 0/6 | 0/6 |
| | Diffuse Large B cell | 0/6 | 0/6 |
| | Burkitt Lymphoma | 0/6 | 0/6 |
| | Hairy Cell Leukemia | 0/6 | 0/6 |
| | Acute Lymphoblastic Leukemia (B-ALL) | 0/6 | 0/6 |
| T cell lymphoma | Anaplastic Large Cell | 1/6 (17%) | 1/1 (100%) |
| | Peripheral, NOS | 13/13 (100%) | 7/13 (54%) |
| | Angioimmunoblastic | 9/9 (100%) | 6/9 (67%) |
| | Acute Lymphoblastic Leukemia (T-ALL) | 5/6 (83%) | 4/6 (67%) |
| Hodgkin lymphoma | Classical | 0/6 | 0/6 |
| | Lymphocyte Predominant | 0/6 | 0/6 |
| Plasma cells neoplasms | Myeloma | 0/6 | 0/6 |
| Acute myeloid leukaemia | | 0/6 | 0/6 |

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for investigating T-cell clonality of a T-cell malignancy in a subject which comprises the step of detecting the expression of TRBC2 by malignant T cells from said subject using a polyclonal antibody which binds the T-cell receptor constant region 2 (TRBC2) intracellular portion having the sequence VKRKDSRG (SEQ ID NO: 1) and which does not cross-react with T-cell receptor constant region 1 (TRBC1) to establish whether malignant T cells from the subject express TRBC2.

2. A method according to claim 1 which comprises the step of investigating TRBC2 expression in a tissue sample from the subject.

3. A method according to claim 2 wherein the sample is a formalin-fixed paraffin-embedded (FFPE) tissue sample.

4. A method according to claim 1 in which TRBC2 expression is investigated using immunohistochemistry.

5. A method for treating a T-cell malignancy in a subject, which comprises the following steps:
   a) investigating the clonality of the T-cell malignancy comprising detecting the expression of TRBC2 by malignant T cells from said subject using a polyclonal antibody which binds the T-cell receptor constant region 2 (TRBC2) intracellular portion having the sequence VKRKDSRG (SEQ ID NO: 1) and which does not cross-react with T-cell receptor constant region 1 (TRBC1), to establish whether malignant T cells from the subject express TRBC2; and
   b) administering a TRBC2-specific therapeutic agent to a subject having a TRBC2-expressing T-cell malignancy, wherein the TRBC2-specific therapeutic agent is a therapeutic antibody, an antibody-drug conjugate, a bispecific T-cell engager, or a chimeric antigen receptor (CAR)-T cell composition.

6. A method according to claim 1, wherein the T-cell malignancy is a T cell lymphoma or leukemia.

7. A method according to claim 6, wherein the T cell lymphoma or leukemia is selected from: peripheral T-cell lymphoma, not otherwise specified (PTCL-NOS); angio-immunoblastic T-cell lymphoma (AITL); anaplastic large cell lymphoma (ALCL); enteropathy-associated T-cell lymphoma (EATL); hepatosplenic T-cell lymphoma (HSTL); extranodal NK/T-cell lymphoma nasal type; cutaneous T-cell lymphoma; primary cutaneous ALCL; T cell prolymphocytic leukaemia and T-cell acute lymphoblastic leukaemia (T-ALL).

8. A method according to claim 5, wherein the T-cell malignancy is a T cell lymphoma or leukemia.

9. A method according to claim 8, wherein the T cell lymphoma or leukemia is selected from: peripheral T-cell lymphoma, not otherwise specified (PTCL-NOS); angio-immunoblastic T-cell lymphoma (AITL); anaplastic large cell lymphoma (ALCL); enteropathy-associated T-cell lymphoma (EATL); hepatosplenic T-cell lymphoma (HSTL); extranodal NK/T-cell lymphoma nasal type; cutaneous T-cell lymphoma; primary cutaneous ALCL; T cell prolymphocytic leukaemia and T-cell acute lymphoblastic leukaemia (T-ALL).

10. A polyclonal antibody preparation which binds T-cell receptor constant region 2 (TRBC2) intracellular portion having the sequence shown as SEQ ID NO: 1 (VKRKDSRG) and does not cross-react with T-cell receptor constant region 1 (TRBC1).

11. A polyclonal antibody preparation according to claim 10, which was obtained by a method which comprises the following steps:
   (i) immunisation of an animal with a peptide comprising the sequence VKRKDSRG (SEQ ID NO: 1);

(ii) isolation of antibodies from the serum of the immunised animal to give a polyclonal antibody preparation; and
(iii) depletion of any TRBC1-reactive antibodies using a peptide comprising the sequence VKRKDF (SEQ ID NO: 2).

* * * * *